United States Patent
Hill et al.

(10) Patent No.: US 10,548,723 B2
(45) Date of Patent: Feb. 4, 2020

(54) PROSTHETIC HEART VALVE DEVICES AND METHODS OF VALVE REPLACEMENT

(71) Applicant: Medtronic, Inc., Minneapolis, MN (US)

(72) Inventors: Alexander J. Hill, Blaine, MN (US); Cynthia Clague, Minnetonka, MN (US); Carol E. Eberhardt, Fullerton, CA (US); Ana Menk, Minneapolis, MN (US); Mark J. Capps, Mission Viejo, CA (US); Billie Millwee, Fullerton, CA (US); Janice Lynn Shay, Lake Forest, CA (US); Debra Taitague, Orange, CA (US); Joseph C. Morrow, Eden Prairie, MN (US); Jerald Redmond, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/793,639

(22) Filed: Oct. 25, 2017

(65) Prior Publication Data

US 2018/0055632 A1    Mar. 1, 2018

Related U.S. Application Data

(63) Continuation of application No. 13/692,577, filed on Dec. 3, 2012, now Pat. No. 9,827,090, which is a
(Continued)

(51) Int. Cl.
*A61F 2/24* (2006.01)

(52) U.S. Cl.
CPC .......... *A61F 2/2412* (2013.01); *A61F 2/2418* (2013.01); *A61F 2/2457* (2013.01);
(Continued)

(58) Field of Classification Search
CPC .......................................... A61F 2/2454–2457
See application file for complete search history.

(56) References Cited

U.S. PATENT DOCUMENTS

| 4,034,850 A | 7/1977 | Mandel et al. |
| 5,344,442 A | 9/1994 | Deac |

(Continued)

FOREIGN PATENT DOCUMENTS

| DE | 200 03 874 | 6/2000 |
| DE | 100 10 074 | 4/2005 |

(Continued)

OTHER PUBLICATIONS

Bolling, et al., "Mitral Valve Reconstruction in the Patient with Heart Failure," Heart Failure Reviews, 6, 177-185, 2001.
(Continued)

*Primary Examiner* — Yashita Sharma
*Assistant Examiner* — Rebecca S Preston
(74) *Attorney, Agent, or Firm* — Medler Ferro Woodhouse & Mills PLLC

(57) ABSTRACT

A stented valve having at least one leaflet made of pericardium or other material having a relatively thin profile at the annulus. The leaflets are attached via chords to a stent frame, where the chords are positioned to mimic the native valve anatomy and functionality. In particular, the valves of one exemplary embodiment of the invention are sized to replace a mitral valve and therefore the chords are arranged to prevent prolapse of the leaflets into the atrium. The stented valve has a relatively short height at its annulus due to the positioning of the chords. In addition, the stented valve is capable of being crimped to a small enough size that it can be delivered to the implantation site via transcatheter delivery systems and methods.

15 Claims, 3 Drawing Sheets

Related U.S. Application Data continuation of application No. 12/429,054, filed on Apr. 23, 2009, now Pat. No. 8,323,336.

(60) Provisional application No. 61/125,235, filed on Apr. 23, 2008.

(52) U.S. Cl.
CPC .............. *A61F 2/24* (2013.01); *A61F 2/2415* (2013.01); *A61F 2/2454* (2013.01); *A61F 2/2463* (2013.01); *A61F 2/2487* (2013.01); *A61F 2210/0014* (2013.01); *A61F 2220/0016* (2013.01); *A61F 2220/0075* (2013.01); *A61F 2230/001* (2013.01); *A61F 2230/005* (2013.01); *A61F 2230/008* (2013.01); *A61F 2230/0045* (2013.01); *A61F 2230/0054* (2013.01); *A61F 2230/0067* (2013.01); *A61F 2230/0076* (2013.01); *A61F 2250/0039* (2013.01)

(56) References Cited

U.S. PATENT DOCUMENTS

| | | | |
|---|---|---|---|
| 5,411,552 | A | 5/1995 | Andersen et al. |
| 6,042,534 | A | 3/2000 | Gellman et al. |
| 6,254,642 | B1 | 7/2001 | Taylor |
| 6,358,277 | B1 | 3/2002 | Duran |
| 6,440,164 | B1 * | 8/2002 | DiMatteo ............. A61F 2/2412 623/1.24 |
| 6,506,197 | B1 | 1/2003 | Rollero et al. |
| 6,726,715 | B2 | 4/2004 | Sutherland |
| 6,746,458 | B1 | 6/2004 | Cloud |
| 6,821,297 | B2 | 11/2004 | Snyders |
| 6,945,996 | B2 | 9/2005 | Sedransk |
| 7,635,386 | B1 | 12/2009 | Gammie |
| 7,704,277 | B2 | 4/2010 | Zakay et al. |
| 2002/0026092 | A1 | 2/2002 | Buckberg et al. |
| 2002/0032841 | A1 | 3/2002 | Gabbay |
| 2003/0078617 | A1 | 4/2003 | Schwartz et al. |
| 2003/0078653 | A1 | 4/2003 | Vesely et al. |
| 2003/0105519 | A1 | 6/2003 | Fasol et al. |
| 2003/0178325 | A1 | 9/2003 | Roshdy et al. |
| 2004/0019374 | A1 | 1/2004 | Hojeibane et al. |
| 2004/0093060 | A1 | 5/2004 | Sequin et al. |
| 2004/0138745 | A1 | 7/2004 | Macoviak et al. |
| 2004/0143323 | A1 | 7/2004 | Chawla |
| 2004/0210303 | A1 | 10/2004 | Sedransk |
| 2004/0210304 | A1 | 10/2004 | Seguin et al. |
| 2005/0075727 | A1 | 4/2005 | Wheatley |
| 2005/0203616 | A1 | 9/2005 | Cribier |
| 2006/0195183 | A1 | 8/2006 | Navia et al. |
| 2006/0229708 | A1 | 10/2006 | Powell et al. |
| 2006/0259137 | A1 | 11/2006 | Artof et al. |
| 2007/0088391 | A1 | 4/2007 | Mcalexander et al. |
| 2007/0118151 | A1 * | 5/2007 | Davidson ......... A61B 17/00234 606/144 |
| 2007/0118154 | A1 | 5/2007 | Crabtree |
| 2007/0173932 | A1 | 7/2007 | Cali et al. |
| 2008/0147183 | A1 | 6/2008 | Styrc |
| 2008/0208328 | A1 | 8/2008 | Antocci et al. |
| 2009/0005863 | A1 | 1/2009 | Goetz et al. |
| 2009/0177274 | A1 | 7/2009 | Scorsin et al. |
| 2009/0276040 | A1 | 11/2009 | Rowe et al. |
| 2009/0281618 | A1 | 11/2009 | Hill et al. |
| 2009/0306768 | A1 | 12/2009 | Quadri |
| 2009/0319037 | A1 | 12/2009 | Rowe et al. |
| 2010/0030330 | A1 | 2/2010 | Bobo et al. |
| 2010/0036479 | A1 | 2/2010 | Hill et al. |
| 2010/0042147 | A1 | 2/2010 | Janovsky et al. |
| 2010/0217382 | A1 | 8/2010 | Chau et al. |

FOREIGN PATENT DOCUMENTS

| | | |
|---|---|---|
| DE | 102007043830 | 4/2009 |
| WO | 98/29057 A1 | 7/1998 |
| WO | 00/47139 A1 | 8/2000 |
| WO | 01/49213 A2 | 7/2001 |
| WO | 03/003949 A2 | 1/2003 |
| WO | 03/047468 A1 | 6/2003 |
| WO | 2005/013860 A2 | 2/2005 |
| WO | 2005/062980 A2 | 7/2005 |
| WO | 2005/067821 | 7/2005 |
| WO | 2005/102015 A2 | 11/2005 |
| WO | 2006/027499 | 3/2006 |
| WO | 2006/070372 A2 | 7/2006 |
| WO | 2006/127765 A1 | 11/2006 |
| WO | 2007/053243 A2 | 5/2007 |
| WO | 2007/071436 | 6/2007 |
| WO | 2008/010817 A1 | 1/2008 |
| WO | 2008/028569 | 3/2008 |
| WO | 2008/029296 A2 | 3/2008 |
| WO | 2008/035337 A2 | 3/2008 |
| WO | 2008/150529 A1 | 12/2008 |
| WO | 2009/033469 | 3/2009 |
| WO | 2009/053497 | 4/2009 |
| WO | 2009/094188 A2 | 7/2009 |
| WO | 2009/094197 A1 | 7/2009 |
| WO | 2009/132187 A1 | 10/2009 |

OTHER PUBLICATIONS

Lozonschi, et al., "Transapical Mitral Valved Stent Implantation," Ann. Thorac. Surg., 2008;86:745-8.

Ma, et al., "Double-crowned valved stents for off-pump mitral valve replacement," Europ. J. of Cardio-thoracic Surg., 28(2005) 194-199.

Massana, et al., "Conservative Surgery of the Mitral Valve. Annuloplasty on a new Adjustable Ring," Cardiovasscular Surgery 1980, 1987: 30-37.

EP Application No. 16194215.6, European Search Report, dated Feb. 15, 2017.

Falk et al., "New Anatomically Oriented Transapical Aortic Valve Implantation," Ann Thorac Surg 2009 87(3):925-6.

Federal Public Service Ministry of Development, Industry and Foreign Trade Brazilian Patent and Trademark Office Report issued in Brazilian Application No. PI0911351-7, dated May 21, 2019.

Opposition Brief issued against European Patent No. EP282700B1, dated Jul. 31, 2017.

Opposition Response to Summons against European Patent No. EP2282700B1, dated Aug. 17, 2018.

Patent Owner Opposition Brief against European Patent No. EP2282700B1, dated Jan. 15, 2018.

Patent Owner Response to Summons against European Patent No. EP2282700B1, dated Aug. 17, 2018.

Summons to attend oral proceedings pursuant to Rule 115(1) EPC in European Application No. 09734094.7, dated Mar. 14, 2018.

* cited by examiner

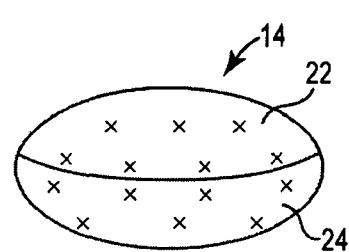
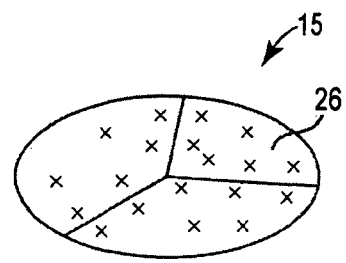
Fig. 1  Fig. 2
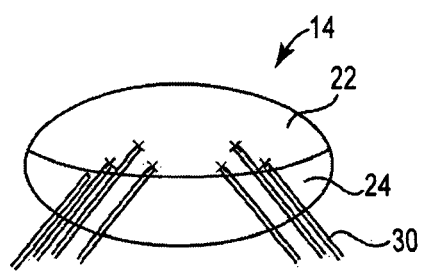
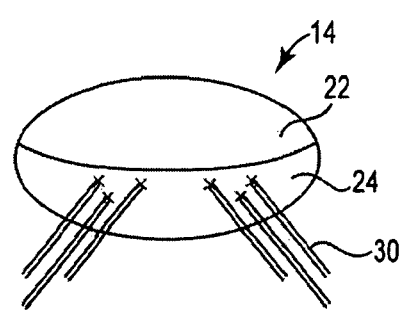
Fig. 3  Fig. 4
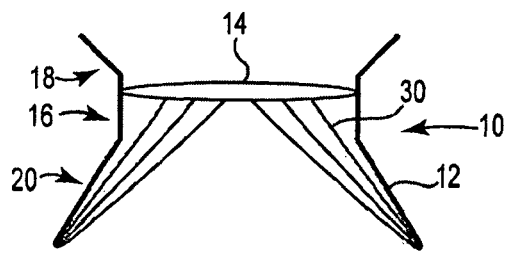
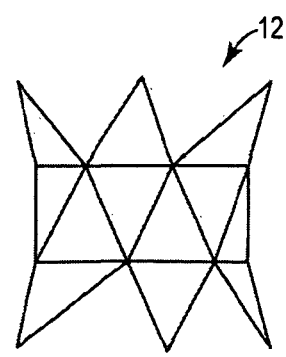
Fig. 5  Fig. 6

PROSTHETIC HEART VALVE DEVICES AND METHODS OF VALVE REPLACEMENT

CROSS-REFERENCE TO RELATED APPLICATIONS

This application is a continuation of U.S. patent application Ser. No. 13/692,577, filed Dec. 3, 2012, which is a continuation of U.S. patent application Ser. No. 12/429,054, filed Apr. 23, 2009, which claims the benefit of U.S. Provisional Patent Application No. 61/125,235, filed Apr. 23, 2008, each of which is incorporated by reference herein in their entirety.

TECHNICAL FIELD

The present invention relates generally to devices and methods for repair of heart valves, and more particularly to prosthetic heart valves for use in replacement of the mitral valve.

One of the two atrio-ventricular valves in the heart is the mitral valve, which is located on the left side of the heart and which forms or defines a valve annulus and valve leaflets. The mitral valve is located between the left atrium and the left ventricle, and serves to direct oxygenated blood from the lungs through the left side of the heart and into the aorta for distribution to the body. As with other valves of the heart, the mitral valve is a passive structure in that it does not itself expend any energy and does not perform any active contractile function.

The mitral valve includes two moveable leaflets that open and close in response to differential pressures on either side of the valve. Ideally, the leaflets move apart from each other when the valve is in an open position, and meet or "coapt" when the valve is in a closed position. However, problems can develop with valves, which can generally be classified as either stenosis, in which a valve does not open properly, or insufficiency (also called regurgitation), in which a valve does not close properly. Stenosis and insufficiency may occur concomitantly in the same valve. The effects of valvular dysfunction vary, with mitral regurgitation or backflow typically having relatively severe physiological consequences to the patient. Regurgitation, along with other abnormalities of the mitral valve, can increase the workload placed on the heart. The severity of this increased stress on the heart and the patient, and the heart's ability to adapt to it, determine the treatment options that are available for a particular patient. In some cases, medication can be sufficient to treat the patient, which is the preferred option when it is viable; however, in many cases, defective valves have to be repaired or completely replaced in order for the patient to live a normal life.

One situation where repair of a mitral valve is often viable is when the defects present in the valve are associated with dilation of the valve annulus, which not only prevents competence of the valve but also results in distortion of the normal shape of the valve orifice. Remodeling of the annulus is central to these types of reconstructive procedures on the mitral valve. When a mitral valve is repaired, the result is generally a reduction in the size of the posterior segment of the mitral valve annulus. As a part of the mitral valve repair, the involved segment of the annulus is diminished (i.e., constricted) so that the leaflets may coapt correctly on closing, and/or the annulus is stabilized to prevent post-operative dilatation from occurring. Either result is frequently achieved by the implantation of a prosthetic ring or band in the supra annular position. The purpose of the ring or band is to restrict, remodel and/or support the annulus to correct and/or prevent valvular insufficiency. Such repairs of the valve, when technically possible, can produce relatively good long-term results.

However, valve repair is sometimes either impossible or undesirable or has failed, such as in cases where dilation of the valve annulus is not the problem, leaving valve replacement as the preferred option for improving operation of the mitral valve. In cases where the mitral valve is replaced, the two general categories of valves that are available for implantation are mechanical valves and bioprosthetic or tissue valves. Mechanical valves have been used for many years and encompass a wide variety of designs that accommodate the blood flow requirements of the particular location where they will be implanted. Although the materials and design features of these valves are continuously being improved, they do increase the risk of clotting in the blood stream, which can lead to a heart attack or stroke. Thus, mechanical valve recipients must take anti-coagulant drugs for life to prevent the formation of thrombus. On the other hand, the use of tissue valves provide the advantage of not requiring anti-coagulant drugs, although they do not typically last as long as a mechanical valve. Traditionally, either type of valve has been implanted using a surgical procedure that involves opening the patient's chest to access the mitral valve through the left atrium, and sewing the new valve in position. This procedure is very invasive, carries risks of infection and other complications, and requires a lengthy period of recovery for the patient.

To simplify surgical procedures and reduce patient trauma, there has been a recent increased interest in minimally invasive and percutaneous replacement of cardiac valves. Replacement of a heart valve in this way typically does not involve actual physical removal of the diseased or injured heart valve. Rather, a replacement valve is delivered in a compressed condition to the valve site, where it is expanded to its operational state. One example of such a valve replacement system includes inserting a replacement pulmonary valve into a balloon catheter and delivering it percutaneously via the vascular system to the location of a failed pulmonary valve. There, the replacement valve is expanded by a balloon to compress the native valve leaflets against the right ventricular outflow tract, thereby anchoring and sealing the replacement valve. In the context of percutaneous, pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. As described in the articles: "Percutaneous Insertion of the Pulmonary Valve," Bonhoeffer, et al., Journal of the American College of Cardiology 2002; 39: 1664-1669 and "Transcatheter Replacement of a Bovine Valve in Pulmonary Position," Bonhoeffer, et al., Circulation 2000; 102: 813-816, the replacement pulmonary valve may be implanted to replace native pulmonary valves or prosthetic pulmonary valves located in valved conduits. Other implantables and implant delivery devices also are disclosed in published U.S. Patent Application Publication No. 2003/0036791 A1 and European Patent Application No. 1 057 460-A1.

Due to the different physical characteristics of the mitral valve as compared to the pulmonary valve, percutaneous implantation of a valve in the mitral position has its own unique requirements for valve replacement. There is a continued desire to be able to be able to improve mitral valve replacement devices and procedures to accommodate the physical structure of the heart without causing undue stress during operation of the heart, such as providing devices and methods for replacing the mitral valve percutaneously.

SUMMARY

One embodiment of the invention includes a pericardial valve with artificial chords or chordae tendinae that closely replicates the native atrioventricular valve anatomy. This is accomplished by constructing a valve of two or more leaflets made of pericardium or other material having a relatively thin profile at the annulus. The artificial chordae can be constructed of ePTFE, for example, and can be attached in a variety of manners to the leaflets. These chords are positioned to mimic the native valve anatomy and functionality. In particular, the valves of one exemplary embodiment of the invention are sized to replace a mitral valve and therefore the chords are arranged to prevent prolapse of the leaflets into the atrium.

The pericardial valve design of the invention advantageously provides a stented valve having a relatively short height at its annulus due to the positioning of the chords. In addition, the stented valves are capable of being crimped to a small enough size that they can be delivered to the implantation site via transcatheter delivery systems and methods.

The stents used for the stented valves of the invention can be compressible and expandable stents for implantation into a body lumen, such as for replacement of one of the atrioventricular valves. The stent of one embodiment of these stented valves comprises a frame having a central annular region, atrial flares extending from one side of the annular region, and ventricular flares extending from one portion of the opposite side of the annular region.

BRIEF DESCRIPTION OF THE DRAWINGS

The present invention will be further explained with reference to the appended Figures, wherein like structure is referred to by like numerals throughout the several views, and wherein:

FIGS. 1 and 2 are top schematic views of a bi-leaflet and a tri-leaflet tissue valve of the invention, respectively, and including multiple chord placement locations;

FIG. 3 is an oblique view of the tissue valve of FIG. 1 and illustrating multiple anterior chords;

FIG. 4 is an oblique view of the tissue valve of FIG. 1 and illustrating multiple posterior chords;

FIG. 5 is a schematic partial cross-sectional view of a tissue valve of the type illustrated in FIGS. 3 and 4 as positioned within a stent frame;

FIG. 6 is a front schematic view of an exemplary stent of the type that can be used with the tissue valves of the invention;

DETAILED DESCRIPTION

Figure 7:
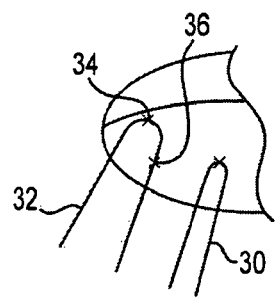
FIG. 7 is an oblique view of a portion of a tissue valve with attached chords.

Referring now to the Figures, wherein the components are labeled with like numerals throughout the several Figures, and initially to FIGS. 1-5, a variety of views of one exemplary embodiment of a stented valve 10 in accordance with the invention is illustrated. Although the stented valves of the invention, such as stented valve 10, are primarily described herein as being used for mitral valve replacement, it is understood that many of the features of these stented valves can be used for valves in other areas of the heart. For example, the stented valves of the invention may be used for replacement of the tricuspid valve, where the configuration of such a stented valve may be identical or slightly different than described herein for replacement of the mitral valve due to the different anatomy in that area of the heart. In any case, the stents and valves of the invention desirably restore normal functioning of a cardiac valve, and are intended for percutaneous implantation to take advantage of the benefits of this type of surgery. However, the stents described herein may instead be implanted using surgical techniques that include minimally invasive methods or more traditional open-heart surgical methods.

Stented valves of the invention, such as stented valve 10, comprise a stent or stent frame and a valve comprising at least one leaflet that is attached within the interior portion of the stent frame using a variety of different stent attachment devices and methods. Exemplary embodiments of the stent frames of the invention are shown and described relative to the figures, such as exemplary stent frame 12. The stent frames used for the stented valves described herein may be fabricated of platinum, stainless steel, Nitinol, superelastic polymers (which in turn could be a shape memory polymer), or other biocompatible metals or combinations of metals. The stent frames may alternatively be fabricated using wire stock, or may be produced by machining or laser cutting the stent from a metal tube, as is commonly employed in the manufacturing of stents. The number of wires, the positioning of such wires, and various other features of the stent can vary considerably from that shown in the figures, while remaining within the scope of the invention.

In any case, the stent frames of the invention are preferably compressible to a relatively small diameter for insertion into a patient, but are also at least slightly expandable from this compressed condition to a larger diameter when in a desired position in the patient. It is further preferable that the process of compressing the stent frames does not permanently deform them in such a way that future expansion thereof would be difficult or impossible. That is, each stent should be capable of maintaining a desired structural integrity after being compressed and expanded. In one preferred embodiment of the invention, the wires that make up each of the stent frames can be formed from a shape memory material, such as a nickel titanium alloy (e.g., Nitinol). With this material, the stent frame can be self-expandable from a contracted state to an expanded state, such as by the application of heat, energy, or the like, or by the removal of external forces (e.g., compressive forces). Alternatively, the stent frame can be made of materials that are expandable via expansion of a balloon or other device that causes the stent frame to move from a compressed condition to an expanded condition. The stent frame should be repeatedly compressible and expandable without damaging the structure of the stent frame. In addition, the stent frame may be laser cut from a single piece of material, as mentioned above, or may be assembled from a number of different components or wires. For these types of stent structures, one example of a delivery system that can be used includes a catheter with a retractable sheath that covers the stent and its associated valve structure until it is to be deployed, at which point the sheath can be retracted to allow the stent frame to expand. Further details of such a delivery process for delivering stented valves of the present invention are discussed in further detail below.

The stented valves described herein comprise one or more valve materials attached within the inner area of the stent frame to form leaflets. These stented valve assemblies of the invention may use pericardial valve material provided in a tricuspid or bicuspid leaflet configuration. These configurations provide additional valve strength in the relatively high-pressure conditions that exist in the mitral valve area of the heart, and can also allow greater flexibility in designing a valve with a particular size and/or shape.

Referring again to FIGS. 1-5, a stented pericardial valve 10 is provided, which is designed to mimic the native anatomy of the atrioventricular cardiac valves. This valve 10 is different from other ventriculo-arterial valves (i.e., semi-lunar valves) in that it depends on tendinous chords 30 (chordae tendinae) to anchor the leaflets to a stent frame and prevent the prolapse of leaflets into the atrium. In this way, the stented valve 10 can advantageously have a relatively short annular height. This can be particularly beneficial for transcatheter valves, as this relatively short annulus height provides a stent that is able to be crimped to a relatively small size, and more closely replicates the function of the native mitral valve. In addition, the small annular height is advantageous for positioning of the valve, as it will fit more tightly around the native valve annulus, thereby forming a better seal. This concept can be used for either bi-leaflet valves, as is illustrated in FIGS. 1 and 3-5, or for tri-leaflet valves, as is illustrated in FIG. 4. In either case, the valve structures include multiple chords 30 attached to or through the surface of the valve leaflets. The artificial chords can be made of ePTFE, for example, and are attached to the surface of the leaflets to prevent prolapse of the leaflets into the atrium.

As is best illustrated in FIG. 5, stented valve 10 generally includes a stent or stent frame 12 and a valve 14 attached within the interior portion of the stent 12. The stent frame 12 generally includes an annular portion 16, an atrial portion 18 extending from one end of the annular portion 16, and a ventricular portion 20 extending from the opposite end of the annular portion 16. Atrial portion 18 includes a wire structure that is shaped to flare or extend radially outward at an angle around the periphery of one end of the annular portion 16. The atrial portion 18 is provided for engagement with one side of the annulus in which the stent frame 12 will be implanted, thus, the atrial portion 18 can be designed with a number of different configurations to meet the different requirements of the locations in which it may be implanted. Ventricular portion 20 also includes a structure that flares or extends radially outward at an angle relative to the annular portion 16. A section of this ventricular portion 20 can be specifically flared relative to the annular portion 16 in order to engage with the aortic leaflet (i.e., the aortic portion of the ventricular flare) but still not substantially block the left ventricular outflow tract. The ventricular portion 20 is provided for particular engagement with an annulus in which the stent frame will be implanted, such as the posterior side of a mitral annulus; however, it should not obstruct the left ventricular outflow tract when implanted in the mitral position.

The stent frame 12 may include a number of wires or wire portions that are attached to each other generally as shown in the illustrated configuration, where one arrangement could include separate wires for each of the annular portion 16, the atrial portion 18, and the ventricular portion 20. Alternatively, the entire stent frame 12 may be cut from a single sheet of material such that the stent frame 12 is an integral structure that does not include individual components. The relative sizes and number of wire peaks, valleys, and flanges illustrated for each of the portions of the stent frame 12 are exemplary, and the construction can instead include different sizes, numbers, and configurations of these components.

When the stented valve is being provided for replacement of the mitral valve, it is typically provided in an elliptical or oval shape, as is illustrated in FIGS. 1-4. In particular, FIGS. 1, 3, and 4 illustrate an exemplary bi-leaflet valve 14 which comprises an anterior leaflet 22 and a posterior leaflet 24. The leaflets 22, 24 can be constructed of pericardium material with a relatively thin profile at the annulus. In the atrial view of a bi-leaflet valve of FIG. 1 and the atrial view of a tri-leaflet valve of FIG. 2, multiple chord placements are illustrated as "X" markings on the leaflets, where the number of chords can be smaller or larger than illustrated. The chords can alternatively or additionally be attached to the edge of the leaflet as well as the body. FIG. 3 illustrates chords 30 extending from the anterior leaflet 22 and FIG. 4 illustrates chords 30 extending from the posterior leaflet 24. FIG. 5 illustrates chords 30 of such a bi-leaflet valve 14 attached to stent frame 12, with the chords 30 attached to both the leaflets of the valve and the ventricular portion 20 of the stent frame 12. In this illustrated embodiment, the ends of the chords are attached at a point of the ventricular portion furthest from the annular portion, however, it is understood that the chords can instead be attached at different locations on the stent frame. The chords may also be attached at one or more levels of the ventricular flares.

Attachment of the multiple chords 30 to the surface of the leaflets can be performed in a number of different types of ways, where a particular stented valve can use one or more different types of attachment methods and/or devices. One attachment method is generally illustrated in FIGS. 3 and 4, in which each chord 30 is passed through the leaflet material in two locations that are at closely adjacent to one another so that both ends of the chord are on the same side of the leaflet and arranged as a pair. When attaching the ends of these chords to a stent frame, each end of the pair can be attached independently to the stent frame at locations that are spaced at least somewhat from each other, or the pair of chord ends can be treated as a single unit and kept together as a pair when being attached to the stent frame.

Another attachment method is illustrated in FIG. 7, which shows a chord 32 entering a leaflet material at a location 34, extending across the opposite side of the leaflet by a distance (shown as a broken line), and then exiting the leaflet material at a location 36. Such a separation of the ends of the chord in this way can distribute the forces and help to prevent possible tearing or ripping of the leaflet material.

Figure 8:
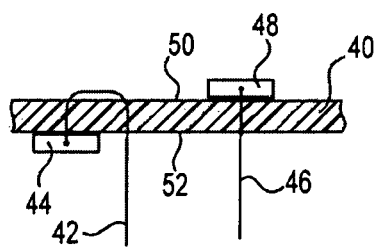
FIG. 8 is a cross-sectional side view of a portion of a tissue valve and illustrating exemplary chord attachment configurations.

Additional attachment methods are illustrated for attaching chords to a leaflet portion 40 in FIG. 8. Leaflet portion 40 includes a first surface 50 and an opposite surface 52. Chord 42 is shown as having one end attached to a piece of material or tab 44 that is positioned against the second surface 52 of the leaflet portion 40. The chord 42 then passes through the leaflet 40, extends across a portion of the first surface 50, then passes back through the leaflet so that its free end extends from the second surface 52. Similarly, chord 46 has one end attached to a piece of material or tab 48 that is positioned against the first surface 50 of the leaflet portion 40. The chord 46 passes through the leaflet 40 so that its free end extends from the second surface 52. A single leaflet may comprise one or both of these chord attachment configurations, or may comprise one or a combination of different chord attachment configurations.

In other alternative arrangements, chords can be attached to leaflets of a valve using sutures, adhesives (e.g., bioadhesives), tissue welding, and the like. The chords may be provided as single structures or may be provided in pairs or larger groupings. The chords may also be provided with different lengths to accommodate certain desired distances between the portion of the leaflet to which they are attached when the valve is in its closed configuration and the stent frame to which the chords are attached. The chords may further be provided with the ability to be adjusted in length, if desired, in order to optimize the performance of the valve, for example.

The chords themselves may be made of a wide variety of materials, which can generally fall into the broad categories of: (1) synthetic or manufactured chords; and (2) harvested or native chords. In either case, the chords should be selected to have certain properties that are desirable and/or necessary for the particular valve in which they will be used. For one example, the chord material can be selected to provide chords that are not subject to fatigue failure, even after very high numbers of cycles under which the chords will be subjected to relatively high stresses. In addition, the chord material can be selected from materials that will not stretch, as the performance of the stented valve will significantly suffer if the chords can stretch or extend far enough that the leaflets will be able to prolapse into the atrium, for example. Examples of materials from which the chords can be made include silk and ultra high molecular weight polyethylene.

The chord material can further be selected to be compatible with the material from which the leaflets are made. As described above, the leaflets may be made of pericardial material; however, the leaflets may instead be made of another material, such as native leaflets obtained from a donor source (e.g., leaflets from a porcine valve), leaflets made from other membranous tissue in the body, such as intestinal submucosa, thin film Nitinol, cloth, or a polymeric material, for example. One polymeric material from which the leaflets can be made is an ultra high molecular weight polyethylene material commercially available under the trade designation "Dyneema" from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

The stented valves of the invention may alternatively be provided with a valve having three or more leaflets, where an exemplary tri-leaflet valve 15 is illustrated in FIG. 2. All of the features and variations described above relative to bi-leaflet valves are also applicable for use with tri-leaflet valves or with valves having more than three leaflets. For example, the valve 15 has three leaflets 26 that are attached along one edge to a stent frame that can be oval or elliptical in shape, for example. Each of the leaflets 26 includes multiple chords extending from their surfaces, where each of the chord placements is illustrated as an "X" marking on the leaflets. Any of the described chord attachment methods described above can also be used for attachment of these chords to the leaflets 26 of the tri-leaflet valve 15.

Figure 9:
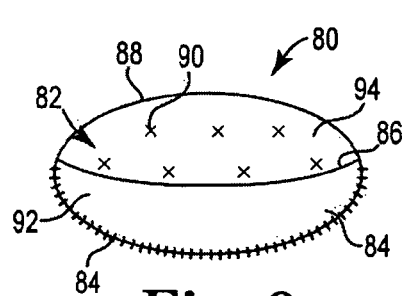
FIG. 9 is a top schematic view of another valve arrangement of the invention.

FIG. 9 is a top schematic view of a stented valve 80 that includes a single piece of leaflet material 82. The leaflet piece 82 is stitched to a stent frame along an edge 84, thereby creating a fixed leaflet portion 92 and a moveable leaflet portion 94. Leaflet portion 94 can move relative to fixed portion 92 along fold line 86, where its free edge closes against a stent edge 88. In order to keep the leaflet portion 94 from prolapsing or moving too far into a vessel, leaflet portion 94 can have multiple chords attached to it using any of the materials and techniques described above, such as at the locations 90 designated by an "X" in the figure.

Figure 11:
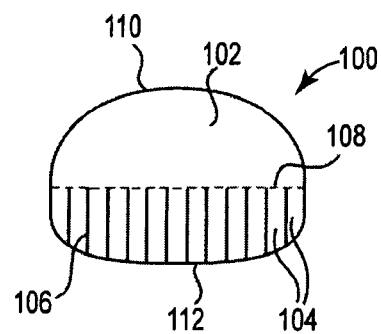
FIG. 11 is a top schematic view of one exemplary leaflet of another valve arrangement of the invention.

FIG. 11 illustrates a leaflet piece 100 that includes another chord attachment arrangement for use with a stent frame. In particular, leaflet piece 100 includes a base portion 102 and multiple chord or attachment portions 104 that are formed by cutting leaflet piece 100 along cut lines 106. In use, the base portion 102 is attached to a stent frame along an attachment edge 110 and the chord portions 104 can be folded downward generally along a fold line 108. The free ends 112 of the chord portions 104 are attachable to a lower portion of a stent frame (e.g., a ventricular portion of a frame) to function to prevent leaflet prolapse, in accordance with the invention.

Figure 12:
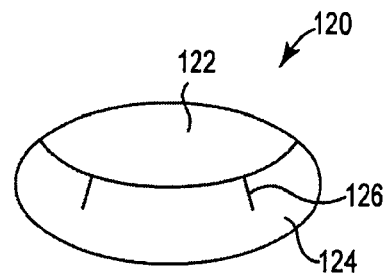
FIG. 12 is a top view of another valve arrangement of the invention, with the leaflets in their closed position.
Figure 13:
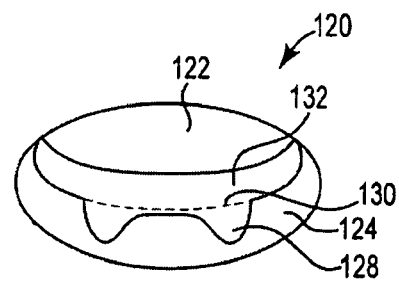
FIG. 13 is a top view of the valve arrangement of FIG. 12, with the leaflets in their open position.

FIGS. 12 and 13 illustrate another valve embodiment 120 that comprises an anterior leaflet 122 and a posterior leaflet 124 that are attached to a stent frame. In this embodiment, posterior leaflet 124 has two gaps or openings along one edge that allow for a more flexible movement of the leaflet 124 during opening and closing of the valve. FIG. 12 shows the leaflets in a closed position and FIG. 13 shows the leaflets in an open position. These Figures illustrate the changes that take place in the stent shape and size during a cardiac cycle. In particular, during filling, the stent will be at its largest shape and the gaps will be open, as is illustrated in FIG. 13 with open gaps 128, an open area 132, and a broken line 130 that generally shows the intersection line of the leaflets when the valve is in its closed position. During systole and ventricular ejection, the stent or supporting structure will deform and potentially become smaller. These gaps will then close, as is illustrated with the closed gap areas 126 of FIG. 12. The gaps thus provide more flexibility to the leaflet during valve movement, which allows the leaflets to coapt more effectively and reduces leakage. In other words, the gaps in the posterior leaflet 124 help to provide a valve that more closely mimics the natural mitral valve morphology and function.

The stented valves of the invention can further include a covering material that is attached to selected wires of the stent frame, and may be attached to all of the wires or wire portions of stent frame, if desired. The covering material can be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. The covering material could also be a natural material such as pericardium or another membranous tissue such as intestinal submucosa. The covering material can be the same material or different than the material from which the leaflets are made. The covering material may be attached to its respective stent frame by sewing, adhesives, or other attachment methods.

Figure 10:
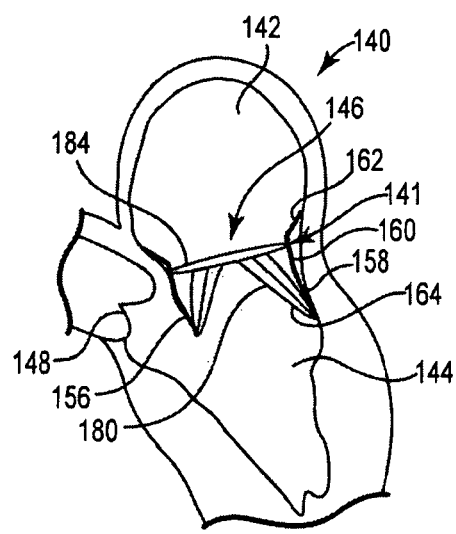
FIG. 10 is a schematic sectional view of a portion of a heart with a stent frame of the invention positioned within the annulus of a mitral valve.

FIG. 10 illustrates a portion of a heart 140, with an exemplary stent assembly 141 of the invention positioned therein. In particular, heart 140 includes a left atrium 142, a left ventricle 144, a mitral valve space 146 and an aortic valve 148. When the native mitral valve is operating properly, the native leaflets will generally function in such a way that blood flows toward the left ventricle 144 when the leaflets are in an open position, and so that blood is prevented from moving toward the left atrium 142 when the leaflets are in a closed position. However, stent assembly 141 can be positioned in the area of mitral valve 146 when it is not functioning properly (to replace the mitral valve) in accordance with the invention, thereby pushing the leaflets out of the mitral valve space, such as are shown as leaflets 156 and 158, respectively.

As shown, stent assembly 141 includes an annular portion 160, an atrial portion 162 extending from one side of the annular portion 160 and toward the left atrium 142, and a ventricular portion 164 extending from the posterior side of the annular portion 160 and toward the left ventricle 144. The stent assembly 141 further includes multiple chords 180, each of which is attached at one end to leaflets 184 and attached at their other end to the stent frame 141. The stent assembly 142 will preferably be configured so that it does not push the leaflet 156 to a position in which it will interfere with blood flow through the aortic valve 148 and/or interfere with the actual movement or functioning of the leaflets of the aortic valve 148. However, annular portion 160 preferably has a sufficient length to provide a suitable area of contact with the annulus of the mitral valve to help to maintain it in its desired position.

As stated above, the stent assemblies of the invention can also be implanted for replacement of the tricuspid valve. In particular, if the stent assemblies of the invention are positioned within the annulus of a triscuspid valve, the atrial portion would be configured in such as way that it would not contact the apex of the triangle of Koch in order to not disturb the conduction system (i.e., the AV node and bundle of His). In addition, the ventricular portion would be configured so that it does not contact the septal portion of the ventricle in order to not disturb the conduction system, wherein these atrial and ventricular portions can thus be similar to those described above relative to stent assemblies for the mitral area.

Stent frames of the type described above can be assembled into a stented valve assembly in accordance with the methods of the invention described herein, although such valves are not shown in the Figures. One exemplary method for assembling a stented valve generally first includes preparation of a pericardial material, then a subsequent mounting or attachment of the pericardial material to the stent frame using a variety of mounting or attachment techniques. Bi-leaflet, tri-leaflet, and other variations of valve assemblies can be attached within the stent frames described herein.

The various flared portions described above relative to the atrial portions and ventricular portions of the stent frames are generally shown (e.g., in FIG. 6) as being V-shaped or U-shaped. However, the flared portions may instead be semi-circular, rectangular, oblong, or the like, and may be considerably smaller or larger than shown. In yet another variation, a different flare structure that is more continuous around the periphery of the annular portion of the stent frame can be used (i.e., the flare structure does not comprise a series of adjacent flares but instead comprises more of a continuous flared structure at one or both ends of the stent frame). In any case, the flare portion(s) are preferably configured to be a shape and size that can provide an anchoring function for the stent assembly when it is positioned to replace a valve. For example, if stent assembly were positioned within the mitral valve annulus any flare portions that extend from the stent assembly on the atrial side can provide interference with the walls of the left atrium, thereby inhibiting motion of the stem assembly.

Any of the embodiments of stent assemblies described herein relative to the invention, may include a gasket or other member around its exterior to provide for sealing against paravalvular leakage and to facilitate pannus in-growth for stabilization of the stent. Such a gasket or other member may alternatively or additionally be positioned on the interior portion of the stent or on the underside of a cuff provided on the stent.

In addition, it is contemplated that the ventricular flares associated with the stented valves of the invention can house biologics to target infarcts (stem cells, genes, proteins, etc.), which are often located posterior-inferiorly in patients with ischemic mitral regurgitation. The areas of the stented valves of the invention used for anchoring could also be seeded with cells or biologics to promote ingrowth for quick incorporation into the surrounding tissue. This could aid in eliminating paravalvular leakage and in eliminating migration or embolization of the prosthesis. In one example for a mitral valve replacement, the atrial and annular portions can include pro-ingrowth biologics and the ventricular portion can include therapeutic biologics and/or pro-ingrowth biologics.

The stent assemblies of the present invention may be positioned within the desired area of the heart via entry in a number of different methods. In one example, the stent assembly may be inserted transatrially, where entry may be done either percutaneously or in a minimally invasive technique on a beating heart in which access is through the side of the heart, or even through a standard open heart valve replacement procedure using heart-lung bypass and sternotomy where the described device would be used as an alternative to the standard replacement. In another example, the stent assembly may be inserted transapically, where entry again may be done either percutaneously or in a minimally invasive technique on a beating heart in which access is through the side of the heart. In yet another example, the stent assembly may be inserted transeptally, where entry can be done percutaneously. In yet another example, the stent assembly is delivered using an antegrade approach in which the ventricular portion of the stent is unsheathed and allowed to expand first, and then positioned at the annulus before releasing the atrial portion of the stent.

The invention further includes a method of positioning a valve into a body lumen, such as one of the atrioventricular valve openings of the heart. The method comprises the steps of compressing a stent frame of a stented valve, wherein the stent frame includes a central annular region, an atrial portion, and a ventricular portion. A sheath or other component of a delivery system can be slid or otherwise positioned over the compressed stented valve to keep it from expanding and to minimize interference between the stented valve and the vasculature through which it will be traveling. The stented valve is then delivered to the annulus of the desired valve area of the patient, which delivery may be performed transapically, for example. In one method, the valve is accessed through the bottom of the valve. When the valve is in position, the atrial region or portion of the stent is released, such as by retracting the sheath of the delivery system by a sufficient amount that this portion of the stented valve is exposed. Due to the self-expanding properties of the stent frame, this atrial portion will expand outwardly relative to the sheath in which it was enclosed. The delivery system is then used to pull the stent valve back against the annulus to engage the atrial portion of the stent with the annulus. The sheath of the delivery system can then be further retracted to release the ventricular portion of the stent frame from the delivery system. Due to the self-expanding properties of the stent frame, this ventricular portion will expand outwardly relative to the sheath in which it was enclosed. The delivery system can then be retracted from the patient.

The present invention has now been described with reference to several embodiments thereof. The contents of any patents or patent application cited herein are incorporated by reference in their entireties. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein.

What is claimed is:

1. A stented valve comprising:
   a stent frame comprising first and second end portions extending from an annular portion, wherein the first end portion is flared radially outwardly relative to the annular portion;
   a prosthetic valve comprising first and second leaflets attached within an interior area of the annular portion, the first and second leaflets each comprising a body portion between a fixed leaflet edge portion and a free edge, the first and second leaflets being movable between an open position and a closed position, the first leaflet and the second leaflet coapting at the closed position; and
   a first chord attached to the body portion of the first leaflet and the first end portion of the stent frame, the first chord being arranged to prevent prolapse of the first leaflet.

2. The stented valve of claim 1, further comprising a second chord attached to the body portion of the second leaflet and the first end portion of the stent frame, the second chord being arranged to prevent prolapse of the second leaflet.

3. The stented valve of claim 2, wherein the prosthetic valve further comprises a third leaflet attached within the interior area of the annular portion, the third leaflet being movable between the open position and the closed position, the third leaflet coapting with the first leaflet and the second leaflet at the closed position; and
   a third chord attached to a body portion of the third leaflet and the first end portion of the stent frame, the third chord being arranged to prevent prolapse of the third leaflet.

4. The stented valve of claim 1, wherein the first chord is adhered to the first leaflet.

5. The stented valve of claim 1, wherein a first end and a second end of the first chord extend from the same side of the first leaflet.

6. The stented valve of claim 5, wherein the first and second ends of the first chord are attached to the first end portion of the stent frame.

7. The stented valve of claim 1, wherein the first chord extends from a first side of the first leaflet to a second side of the first leaflet.

8. The stented valve of claim 1, wherein the first leaflet and second leaflet comprise pericardial material.

9. The stented valve of claim 1, wherein the first chord comprises a synthetic material.

10. The stented valve of claim 1, wherein the stent frame is compressible and expandable for percutaneous delivery and implantation into a body lumen.

11. The stented valve of claim 1, wherein the stent frame comprises a shape memory material.

12. The stented valve of claim 1, further comprising a covering material attached to at least a portion of the annular portion.

13. The stented valve of claim 1, wherein the first chord comprises a first end attached to a tab member, wherein the tab member is adjacent to a first surface of the first leaflet.

14. The stented valve of claim 1, wherein the second end portion flares radially outward relative to the annular portion.

15. The stented valve of claim 1, wherein the first chord passes through the body portion of the first leaflet at two locations closely adjacent to each other.

* * * * *